United States Patent
Kayser et al.

(10) Patent No.: US 7,835,057 B2
(45) Date of Patent: *Nov. 16, 2010

(54) METHOD OF CALIBRATING LIGHT DELIVERY SYSTEMS, LIGHT DELIVERY SYSTEMS AND RADIOMETER FOR USE THEREWITH

(75) Inventors: Roy Kayser, Oakville (CA); Yu Song, Richmond Hill (CA); Mitchell Wade MacDonald, Mississauga (CA)

(73) Assignee: EXFO Photonic Solutions Inc., Mississauga (CA)

( * ) Notice: Subject to any disclaimer, the term of this patent is extended or adjusted under 35 U.S.C. 154(b) by 486 days.

This patent is subject to a terminal disclaimer.

(21) Appl. No.: 12/071,682

(22) Filed: Feb. 25, 2008

(65) Prior Publication Data

US 2008/0197300 A1 Aug. 21, 2008

Related U.S. Application Data

(63) Continuation-in-part of application No. 11/312,462, filed on Dec. 21, 2005, now Pat. No. 7,335,901.

(60) Provisional application No. 60/638,344, filed on Dec. 23, 2004.

(51) Int. Cl.
*G02F 1/03* (2006.01)

(52) U.S. Cl. .............. 359/246; 359/227; 250/504 R; 250/493.1

(58) Field of Classification Search ............ None
See application file for complete search history.

(56) References Cited

U.S. PATENT DOCUMENTS

| | | | |
|---|---|---|---|
| 5,029,957 A | 7/1991 | Hood | |
| 5,115,761 A | 5/1992 | Hood | |
| 5,521,392 A * | 5/1996 | Kennedy et al. | 250/492.1 |
| 5,757,425 A * | 5/1998 | Barton et al. | 348/241 |
| 6,355,935 B1 | 3/2002 | Kalley et al. | |
| 6,755,647 B2 | 6/2004 | Melikechi et al. | |
| 6,847,170 B2 | 1/2005 | Kayser | |

(Continued)

*Primary Examiner*—Bernard E Souw
*Assistant Examiner*—Andrew Smyth
(74) *Attorney, Agent, or Firm*—Thomas Adams

(57) ABSTRACT

In a method of calibrating a light delivery device (10) having a solid state light source (12), for example comprising LEDs of an LED array, and an intensity control unit (16) comprising LED array driver and a dimmer module for generating a control signal for controlling at least the intensity of the light source, the light source is temporarily connected by a light guide (24; 24, 26) to a radiometer (38) for detecting irradiance of the delivered light. The light delivery device has a memory (30) for storing control signal parameters and associated radiance levels. The light delivery device is calibrated by adjusting the control signal parameters, e.g. a PWM duty cycle of a control signal to each of a series of predetermined settings, obtaining from the radiometer a corresponding series of delivered light irradiance levels measured thereby, storing the irradiance levels and associated control signal parameters in memory, and applying a best fit algorithm to the irradiance measurements and control signal parameters. Thereafter, a desired irradiate level can be set by selecting the best fit control signal parameters, such as duty cycle of a PWM control or other parameters. Output intensity levels may be measured at the same time as the irradiance levels and used to compensate for light source output level changes when setting a desired irradiance level.

37 Claims, 4 Drawing Sheets

U.S. PATENT DOCUMENTS

| | | |
|---|---|---|
| 7,173,266 B2 | 2/2007 | Katsuki |
| 7,250,611 B2 | 7/2007 | Aguirre et al. |
| 7,335,901 B2 * | 2/2008 | Kayser et al. ........... 250/504 R |
| 2002/0047546 A1 | 4/2002 | Kayser |
| 2004/0080938 A1 * | 4/2004 | Holman et al. ............... 362/231 |
| 2004/0084627 A1 * | 5/2004 | Danilychev ................. 250/372 |
| 2006/0139722 A1 * | 6/2006 | Kayser et al. ............... 359/246 |

* cited by examiner

METHOD OF CALIBRATING LIGHT DELIVERY SYSTEMS, LIGHT DELIVERY SYSTEMS AND RADIOMETER FOR USE THEREWITH

CROSS REFERENCE TO RELATED APPLICATION

This application is a Continuation-in-Part of U.S. patent application Ser. No. 11/312,462 filed Dec. 21, 2005 now U.S Pat. No. 7,335,901 and claims priority from U.S. Provisional patent application No. 60/638,344 filed Dec. 23, 2004; the entire contents of each these prior applications are incorporated herein by reference.

TECHNICAL FIELD

The invention relates to methods of calibrating light delivery systems, to the light delivery systems themselves and to radiometers for use therewith and is especially, but not exclusively, applicable to light delivery systems for printing and curing photosensitive materials including inks, adhesives and other coatings.

BACKGROUND ART

As discussed in the background section of U.S. Pat. No. 5,521,392 (Kennedy et al.), commonly owned with the present invention, there are numerous substances which are sensitive to light energy. The substances of interest generally fall into two classes. The first class comprises substances which undergo polymerization in response to applied light energy. The second class comprises substances which produce a "singlet oxidation molecule" in response to applied light energy. The second class of substances can be found in "photodynamic therapy" or "phototherapy" applications, while the first class of photo-sensitive substances are typically found in UV polymerization and photochemical curing of adhesives.

It is known that the time it takes to cure a photosensitive material, such as an adhesive, ink or other coating is influenced by two principal factors. The first factor encompasses the type of photosensitive material and amount which is required for the application. Once determined for the particular application, this factor remains fixed for the application. The second factor affecting the cure time involves the amount of light energy being delivered to the cure the adhesive. It is also known that the intensity of the light produced by the light source may decrease over the life of the source or be affected by environmental conditions. If the light source degrades, so will the amount of light energy being delivered to cure the adhesive and therefore a longer exposure time is needed to properly cure the adhesive.

In some applications, it may be desirable to adjust the intensity level instead of the exposure time in order to provide a light energy output which is optimum for a particular curing application. Moreover, it is usually desirable to be able to compensate for changes in the light intensity levels caused by the aforementioned environmental changes or the light source degrading throughout its useful life.

Similarly, for printing applications, curing of a uv-curable ink is also influenced by two principle factors. The first factor encompasses the formulation of the ink and amount of UV light which is required for the application, i.e. full cure, pinning, coating, or other application. Once determined for the particular application, this factor remains fixed for the application. The second factor affecting the cure time involves the amount of UV light energy being delivered to cure the UV ink. It is also known that the intensity of the UV light produced by a UV light source, i.e., a conventional lamp, will decrease over the life of the light source. While a UV LED light source does not degrade in the same way, the intensity of both types of UV light source is sensitive to changes in environment, such as temperature changes. If the intensity decreases, the amount of UV light energy being delivered decreases and the intensity or exposure may need to be adjusted.

In some UV curing applications (i.e., full cure, pinning, coating, etc), it may be desirable to adjust the UV intensity level instead of the exposure time in order to provide a UV light energy output which is optimum for the particular UV curing application. Moreover, it is usually desirable to be able to compensate for changes in the UV light intensity levels produced by the UV LED light source which degrades throughout its useful life. U.S. Pat. No. 5,521,392 describes a light curing system for use with such photosensitive materials which provides continuous intensity monitoring and adjusts the exposure time or intensity level, or both, to compensate for output degradation in the light source and thereby provide a constant light energy output, from the curing system, for a given iris setting. The intensity level is measured at the output of a light delivery means of the light curing system. This signal is used by a controller to calibrate the internal continuous monitoring sensor. This allows the internal sensor to be calibrated periodically against a NIST traceable device.

It is desirable to calibrate each radiometer off-site according to industry standards, so each radiometer is detachable so that it can be removed for calibration and replaced temporarily with a spare radiometer which has already been calibrated. In a production setting, there may be many light curing systems and hence many radiometers, especially when the substitutes are included, Calibration of these multiple radiometers is not only time-consuming but also may lead to undesirable differences between the output intensity levels.

In a production setting, there is usually a need for a high degree of consistency between the output intensity levels of the curing systems. Different rates of degradation of the light sources, and transmission losses of the light guides, the different responses of light sources to environmental conditions, as well as different rates of drift of the radiometers, may lead to undesirable differences between output intensity levels of the different light curing systems.

The problem is compounded where several light curing systems are preset to the same output intensity or irradiance setting. As the light curing system degrade or respond differentially, these settings may no longer be the same and may require re-calibration, typically at least once per week and possibly every day.

DISCLOSURE OF INVENTION

The present invention seeks to eliminate, or at least mitigate, the disadvantages of the prior art, or at least provide an alternative.

The above-referenced U.S. parent patent application Ser. No. 11/312,462 discloses and claims a method of setting an output level of a light delivery device (10) that comprises light-emitting means (12), light output means (24; 24, 26) for delivering emitted light to a site to be irradiated, intensity control means (16) for adjusting at least the intensity of the delivered light, and a memory unit (30) for storing data including parameters indicative of intensity/power level, the light output means (24; 24, 26) being temporarily connected to a separate radiometer (38) having means for detecting power levels of the delivered light, the light delivery device (10) and the radiometer (38) having respective control means (28, 48) and data communications means (34, 36, 54, 56) for communicating data therebetween, the method comprising a calibration sequence comprising the steps of:—

(i) with the light output means (24; 24, 26) coupled to the radiometer (38), establishing data communications between the control means (48) of the radiometer (38) and the control means (28) of the light delivery device (10);

at the light delivery device (10):
(ii) adjusting the intensity control means (16) successively to each of a series of predetermined intensity levels;

at the radiometer (38):
(iii) measuring a series of actual output irradiance levels delivered by the light output means (24; 24, 26), each for a respective one of said predetermined intensity levels;
(iv) transmitting the actual output irradiance levels to the light delivery device (10);

at the light delivery device (10):
(v) associating each of the actual output irradiance level measurements with the corresponding intensity level parameters in said memory unit.

In some embodiments, the light source means comprises a conventional lamp, and intensity control means comprises, for example, a variable aperture or shutter.

According to one aspect of the present invention, there is provided a method of setting an output level of a light delivery device (10) that comprises solid state light-emitting means (12), light output means (24; 24, 26) for delivering emitted light to a site to be irradiated, intensity control means (16) for generating a control signal for adjusting at least the intensity of the delivered light, and a memory unit (30) for storing data including parameters of the control signal indicative of intensity/power level, the light output means (24; 24, 26) being temporarily connected to a separate radiometer (38) having means for detecting power levels of the delivered light, the light delivery device (10) and the radiometer (38) having respective control means (28, 48) and data communications means (34, 36, 54, 56) for communicating data therebetween, the method comprising a calibration sequence comprising the steps of:—

(i) with the light output means (24; 24,26) coupled to the radiometer (38), establishing data communications between the control means (48) of the radiometer (38) and the control means (28) of the light delivery device (10);

at the light delivery device (10):
(ii) adjusting the intensity control means (16) successively to set parameters of the control signal corresponding to each of a series of predetermined intensity levels;

at the radiometer (38):
(iii) measuring a series of actual output irradiance levels delivered by the light output means (24; 24, 26), each for a respective one of said predetermined intensity levels;
(iv) transmitting the actual output irradiance levels to the light delivery device (10);

at the light delivery device (10):
(v) associating each of the actual output irradiance level measurements with the corresponding control signal parameters in said memory unit.

Thus, where the light source means comprises a solid state light emitting device, e.g., individual LEDs or groups of LEDs in the form of at least one LED array, rather than a conventional lamp source, the intensity control means (16) typically comprise electronic control means, for example an LED array driver (20) and a distributed dimmer system including a dimmer module (18) providing a control signal for controlling the optical output, including intensity control, of individual LEDs or groups of LEDs of an LED array, or groups of LED arrays. Optionally a shutter module (21) may be also be provided.

Thus the step of adjusting the intensity control means (16) successively to each of a series of predetermined intensity levels may comprise setting control signal parameters of the control signal generated by the dimmer module, e.g. setting parameters of a pulse width modulated (PWM) modulated control such as duty cycle or other parameters of the control signal generated by the dimmer module, for each of a series of different values corresponding to different intensities and storing stored parameters for the control signal corresponding to each of the intensity levels.

In preferred embodiments, the radiometer carries out steps (iii) and (iv) in response to a request from the light delivery device.

Preferably, when establishing communications, the radiometer acquires from the light delivery device a unique identifier, such as its serial number, and associates the irradiance readings with that unique identifier.

The radiometer may have means for determining the dimensions, e.g., diameter, of the light delivery means at its end coupled to said radiometer, the detected power and the dimensions (e.g., diameter) then being used to compute the irradiance of the delivered light, the computed irradiances being said actual irradiance levels.

The radiometer may store effective dimensions (e.g., diameters) of a plurality of different types of light delivery means indexed to a plurality of indicators each unique to a corresponding said type, light delivery means of a particular type having the same effective dimensions (e.g., diameter), and the step of determining the dimensions (e.g., diameter) then may comprise detecting a said unique indicator of said light delivery means connected to the optical input port and using the detected indicator to retrieve the effective dimensions (e.g., diameter) for that light delivery means from storage.

The unique indicator may be colour, and detection of said unique indicator then may comprise the step of determining the colour of a colour-coded adapter connecting the light delivery means to the optical input port, for example by means of a colorimeter in the radiometer.

According to a second aspect of the invention, there is provided a method of setting respective output light irradiance levels of a plurality of light delivery devices to the same irradiance level using the same radiometer, each light delivery device comprising solid state light-emitting means, output means for supplying the emitted light to a site to be irradiated, intensity control means (16) for generating a control signal and selecting parameters of the control signal for adjusting at least the intensity of the delivered light, a memory unit for storing parameters indicative of intensity levels and control means for controlling the intensity control means, the radiometer having data storage means for storing data including light irradiance values, the radiometer and light delivery devices having data communications means for communicating data therebetween, the method comprising the steps of:—

(i) selecting parameters of the control signal for a first light delivery device to deliver a desired irradiance level at its output means;
(ii) temporarily coupling the radiometer to the output means of the first light delivery device and measuring said desired irradiance level;
(iii) storing the control signal parameters associated with said desired irradiance level in the memory of the radiometer;

(iv) temporarily coupling the radiometer to the output means of at least a second such light delivery device, and transmitting said desired irradiance level to said second delivery device via said data communications means; and (v) storing the light irradiance value in the memory of the second light delivery device for future use in normal operation.

Steps (iv) and (v) maybe repeated for a plurality of other such light delivery devices.

Each of the light delivery devices may have means for monitoring for variations in light output of its light-emitting means and the method may include the step of correcting the subsequent control signal parameters for specific intensity levels to compensate for variations in said light output.

The data communications link may be established by way of wireless input/output ports of each light delivery device and radiometer, respectively.

According to a third aspect of the invention, there is provided a radiometer for use in setting output light delivered by at least one light delivery device to a desired light irradiance level, said at least one light delivery device comprising solid-state light emitting means, light output means for supplying the emitted light to a site to be irradiated, intensity control means for generating a control signal and selecting control signal parameters for adjusting at least the irradiance of the delivered light a memory unit for storing irradiance levels, and data communications means, the radiometer comprising:

means for measuring an irradiance level of light delivered by said light output means of said light delivery device;

data communications means complementary to the data communications means of the light delivery device; and control means for establishing data communications with a light delivery device coupled thereto and for outputting to said light delivery device a control signal having control signal parameters for said desired light irradiance value from said memory via the data communications means.

The radiometer may further comprise a storage unit for storing irradiance readings for one or more light delivery devices, indexed according to, for example, serial number of the light delivery device and the date/time of measurement.

The data communications means preferably are wireless.

The radiometer may have means for identifying that the light delivery means coupled to said radiometer has a particular dimensions (e.g., diameter), and the control means may then use the detected power and the dimensions (e.g., diameter) to compute the irradiance of the delivered light, the computed irradiances being said actual irradiance levels.

The unique indicator may be colour, and detection of said unique indicator then may comprise the step of using a colorimeter in the radiometer to detect the colour of a colour-coded adapter connecting the light delivery means to the optical input port.

According to a fourth aspect of the invention, there is provided a light delivery device comprising solid state light-emitting means, light output means for delivering the emitted light to a site to be irradiated, intensity control means comprising a dimmer control system for adjusting irradiance of delivered light; and control means for controlling the intensity control means and for communicating with an external radiometer, the control means being operable to adjust parameters of a control signal for controlling intensity, successively, to a plurality of intensity levels and, for each intensity level, communicate with the radiometer to obtain from the radiometer a corresponding series of actual irradiance levels measured by the radiometer and store each irradiance value in a memory unit in association with the corresponding intensity level.

Where the light source means comprises individual LEDs or groups of LEDs of an LED array, the e intensity control means (16) may comprise an LED array driver, and a dimmer module, for example comprising a pwm control signal generator unit (18) for selecting each of a series of control (dimming) signal parameters to set the intensity level of the optical output of the LED array, the stored parameters then comprising pwm parameters associated with different output intensities of the LED array. The control signal parameters may, for example, include a duty cycle of a PWM control signal.

The intensity control unit may further comprise a shutter module which functions as a switch and may compensate for switching delays associated with switching on and off LEDs of the LED array. Such delays may be a factor when determining exposure times.

The foregoing and other objects, features, aspects and advantages of the present invention will become more apparent from the following detailed description, in conjunction with the accompanying drawings, of a preferred embodiment of the invention which is described by way of example only.

DETAILED DESCRIPTION OF PREFERRED EMBODIMENTS

Figure 1:
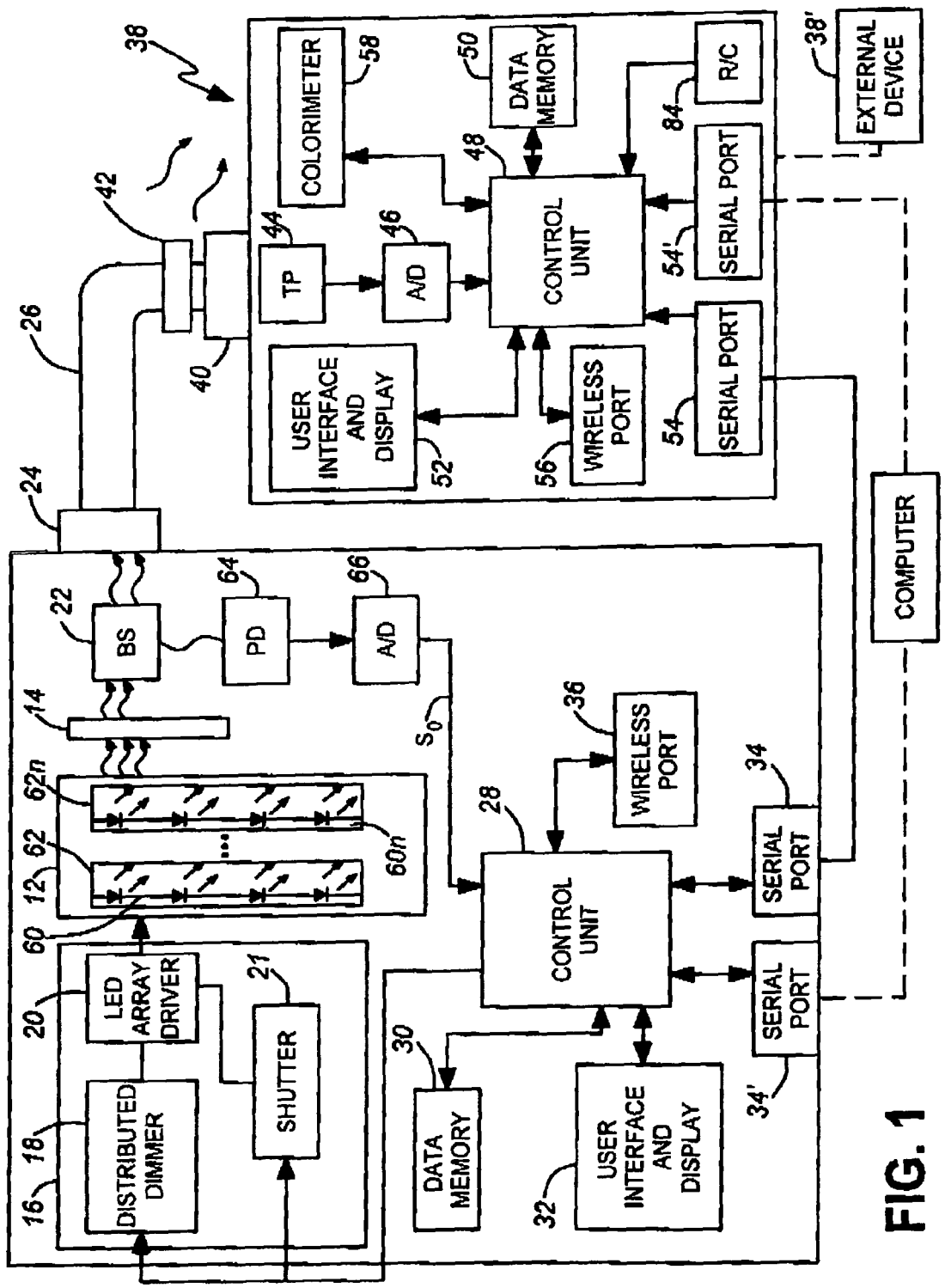
FIG. 1 is a block schematic diagram illustrating a light delivery system comprising a light delivery device and a radiometer temporarily coupled to it.

FIG. 1 illustrates a light delivery system comprising a light delivery device 10, for example a UV printing or spot airing device, which, typically, is one of a set of similar such light delivery devices, perhaps disposed along the same production line. The light delivery device 10 comprises a light source unit 12, a bandpass filter 14, an intensity control module 16. The intensity control module 16 comprises a LED array driver 20, comprising a distributed dimmer module 18, and an electronic shutter control 21. Also provided at the output of the bandpass filter 14 are abeam splitter 22 and an output port 24 to which, in use, a light delivery means 26, specifically a light guide, can be connected. In this embodiment, the light source unit 12 comprises a UV LED light source comprising a plurality (n) of LED arrays 60, . . . 60n, each in a reflective LED array housing 62 . . . 62n. Each UV LED array comprises an array of a plurality of individual LEDs, and the LED array driver and distributed dimmer provides for controlling the optical output from the UV LED array, including controlling the optical output of individual LEDs or groups of LEDs of each LED array 60, . . . 60n of a group of LED arrays. That is, the distributed dimmer 18 and LED Array driver 20 for controlling optical outputs of the individual LEDs or groups of LEDs of the LED array, for example using the duty cycle of pulsewidth modulation (PWM) as the control signal to LEDs of one or more LED arrays, and thereby set the intensity of the optical output, and duration of the optical output from the LEDs of the LED arrays. The distributed dimmer 18 may comprise a PWM signal Generator which is controlled by a control unit 28 which comprises one or more processors and an associated data memory unit 30 and is programmed (e.g. firmware) to control the operation of the light delivery device 10. The control unit 28 is coupled to a user interface and display it 32, whereby a user can input commands and the control unit 28 can display information. The control unit 28 also is coupled to an serial pot 34 and a wireless port 36, through eider of which ports it can communicate with an external radiometer 38. The control unit 28 may also be coupled to an additional serial port 34' for connection to an external computer (86), as shown in broken lines in FIG. 1.

The light output of LED arrays 60, . . . 60n may change in response to environmental, e.g., temperature, changes so the light delivery device 10 includes an intensity control system, specifically a feedback control system for correcting settings of the intensity control module 16 to compensate. The feedback control system includes the beam splitter 22 which, conveniently, is an angled quartz plate with anti-reflection coatings and which taps off 1-2% of the light passing through it and supplies it to a photodetector 64. The corresponding electrical signal from the photodetector 64, which is proportional to the power of the light at the output port 24, is converted by an A-D converter 66 to a corresponding digital signal $S_0$ which is supplied to the control unit 28. If the output of the LED array 60 changes, the control unit 28 will apply a suitable correction when setting the dimming signal of the dimming unit 18 so as to ensure that the light delivered to the proximal end of the light guide 26 has the required intensity level to provide a desired irradiance at the distal or output end of the light guide 26. LED Driver 20 is controlled by a dimmer module which generates a control signal, and may, for example, comprise a PWM control signal generator. Although in this embodiment the distributed dimmer comprises a PWM signal generator, which provides a convenient way of controlling the optical output of the LED array through selecting parameters of a duty cycle (e.g. % duty cycle), in other embodiments, other forms of signal generator using other modulation schemes capable of controlling the optical output of the LED array may alternatively be used to control other parameters of the control signal.

The user interface and display unit 32 typically includes a light emitting diode (LED) display and a set of pushbuttons for selecting a particular mode of operation, and for adjusting the value of a particular parameter according to selected mode. For example, these buttons allow the user to adjust the setting of the exposure time and the intensity level, and store readings. The interface 32 unit may also include a series of indicator lights which are illuminated according to the operation of the pushbuttons and state of the unit. For example, indicator lights may indicate that the LED array 60 is energized and the electronic shutter is open.

When the mode selection pushbutton is operated to select a mode, the light delivery device 10 will be set to one of two modes, conveniently designated "relative" and "absolute". If the light delivery device 10 has not been calibrated, which is the case whenever the light guide has been removed and replaced, the system will be in "relative" mode, and the display will show the dimmer setting or settings indicative of intensity of the optical output as a percentage of PWM duty cycle for maximum optical intensity. Dimmer Seth may be defined in terms of duty cycle, pulse length, amplitude or other parameters of the control signals. If the light delivery device 10 has been calibrated, as will be described later, the system will be in "absolute" mode and the display will show a calibrated intensity level of the light passing through the beamsplitter 22 which is displayed as irradiance in $W/cm^2$. The user may change the level by operating pushbuttons until a desired percentage or irradiance level is displayed. Likewise, with the device set to "Timer" mode, the user may operate pushbuttons to adjust the desired exposure time, specifically by setting a timer in the control unit 28.

The radiometer 38 comprises an optical input port 40 to which the light guide 26 is coupled by an adapter 42. Detection means 44, in the form of a thermopile 44 disposed adjacent the port 40, detects the power of the light from toe light guide 26 and supplies corroding electrical signals to an analog-to-digital converter 46, which supplies the corresponding digital signal $S_{LG}$ to a control unit 48 of the radiometer 38. A data memory 50 coupled to the control unit 48 stores data records and other information associated with the calibration of the light delivery device 10 (and other delivery devices).

The radiometer 38 also comprises a user interface and display unit 52, for communicating commands and information between a user and its own control unit 48, and two input/output data ports, specifically a serial port 54 and a wireless port 56, for connection to the corresponding data ports 34 and 36, respectively, of the light delivery device 10 to enable the exchange of data and signalling between the two control units 28 and 48. The two data ports allow the system to be operated in either a wireless mode or via a conventional cable connection. It should be noted that only one of the data ports need be used at any given time. A Remote Input Connector (RIC) data port 84 is provided to interface the radiometer 38 with other external radiometer devices 38'. The Serial port 54' may also be used for connection with an external computer 86.

In most applications, the light guide 26 comprises a fiber optic cable or a liquid light guide which can be maneuvered around the work piece, either manually or by machine, e.g. a robotic arm.

Figure 2:
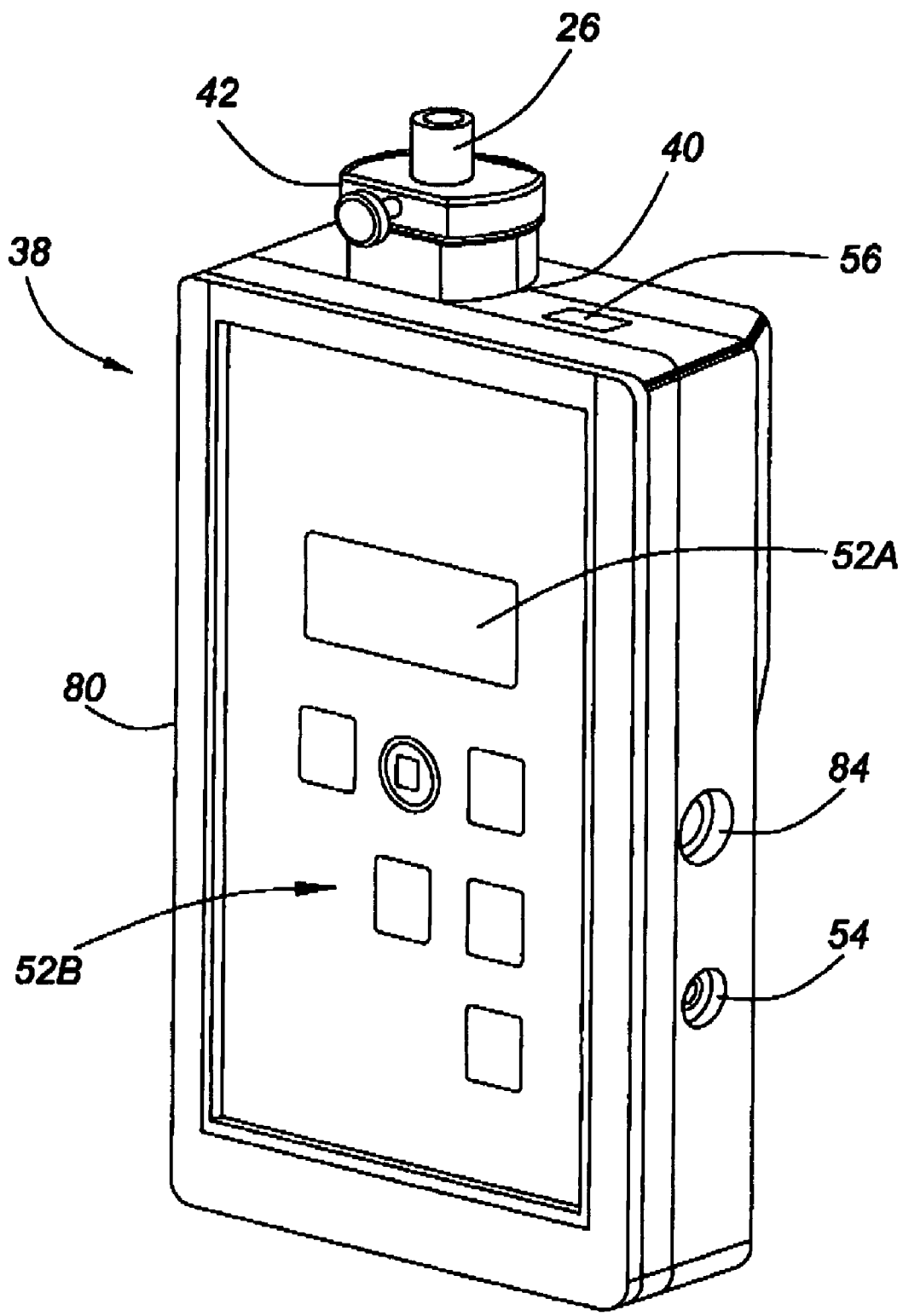
FIG. 2 is a perspective view of the radiometer.

Referring now to FIG. 2, the radiometer 38 comprises a housing 80 with a front panel having the user interface and display unit 52 (FIG. 1), which comprises a liquid crystal display (LCD) 52A and a series of membrane switches 52B for controlling the following modes and function:

RELATIVE/ABSOLUTE for selecting the relative and absolute display modes alternatively (where, in absolute mode, the radiometer 38 displays actual irradiance values and, in relative mode, it displays irradiance values as percentages of a reference value that may be the power at the point of entering relative mode);

CAL for setting up and calibrating compatible delivery devices to a specified irradiance; POWER/IRRAD for toggling between power and irradiance measurements;

EXTERNAL for enabling the radiometer 38 to detect and measure external radiometer devices when connected via a remote input connector (RIC) 84;

STORE to save measurement data into a data log in memory 50 for furniture retrieval by a personal computer via data port 54; and ON for tuning the radiometer 38 on.

The optical input port 40 and adapter 42 protrude from the top of the housing 80. The wireless port 56 also is provided on the top of the radiometer 38, adjacent port 40. (If desired, when the R2000 is coupled to a separate computer (second serial connection), the keypad could be disabled).

Typically, the radiometer 38 will be used with light delivery devices having different light guides, whose lengths and, more importantly, dimensions (e.g., diameters) and, hence, cross-sectional areas may differ. Light guides 26 having the same cross-sectional area will each have the same type of connector, requiring a specific adapter to connect it to the port 40, Light guides having a different dimension (e.g., diameter) will have a different type of connector and hence different adapter. Thus, there are several adapters, each colour-coded with a different colour that identifies the type of light guide 26 with which it is used, and hence represents the dimension/diameter/area. The colour of each adapter is analysed by a colorimeter 58 which is disposed adjacent the port 40. The calorimeter 58 briefly illuminates a section of the adapter 42 with a white LED and, using a colour detection integrated circuit detects the colour and conveys corresponding RGB colour values to the control unit 48. The latter uses the RGB colour values to access its memory 50 and retrieve the corresponding area, the different adapter RGB colour values and associated areas having been previously stored therein during manufacture. Typically, the radiometer 38 will detect and store the diameter/area of the light guide whenever the radiometer 38 is turned ON and/or when a light guide adapter is installed.

In normal use, with the radiometer 38 removed, the light delivery device 10 provides a pre-determined amount of light energy to a work piece or object (not shown) to be treated. The work piece may include a photosensitive material which reacts to the applied light energy. The control unit 28 controls the amount of light energy applied to the work piece according to pre-selected parameters determined from data inputted by the separate radiometer 38, as will be described later, while it is temporarily coupled to the light delivery device 10 by means of a cable connected between Serial ports 34 and 54 of the light delivery device 10 and radiometer 38, respectively (or by a wireless link if preferred). The radiometer 38 will usually have been calibrated off-site according to industry standards (e.g. NIST).

As mentioned above, if the light delivery device has not been calibrated, its PWM settings will be determined as a percentage of maximum PWM duty open area and the control unit 28 will calculate and issue corresponding control signal parameters to the intensity control module 16 according to inputs via the user interface and display unit 32 or from the radiometer 38.

If the light delivery device 10 is to be used in absolute mode, as explained previously, it must be calibrated so that a user, either manually or by way of a radiometer, can input a desired radiance and the light delivery device 10 will operate the intensity control module 16 to select the parameters of the control signals, for example to set the PWM duty cycle of the control signal required to deliver that irradiance level at the end of the light guide 26. In fact, even if the light delivery device 10 has been calibrated, whenever certain critical things change for example the light guide or the LED array, another calibration process will need to be carried out.

Figure 3:
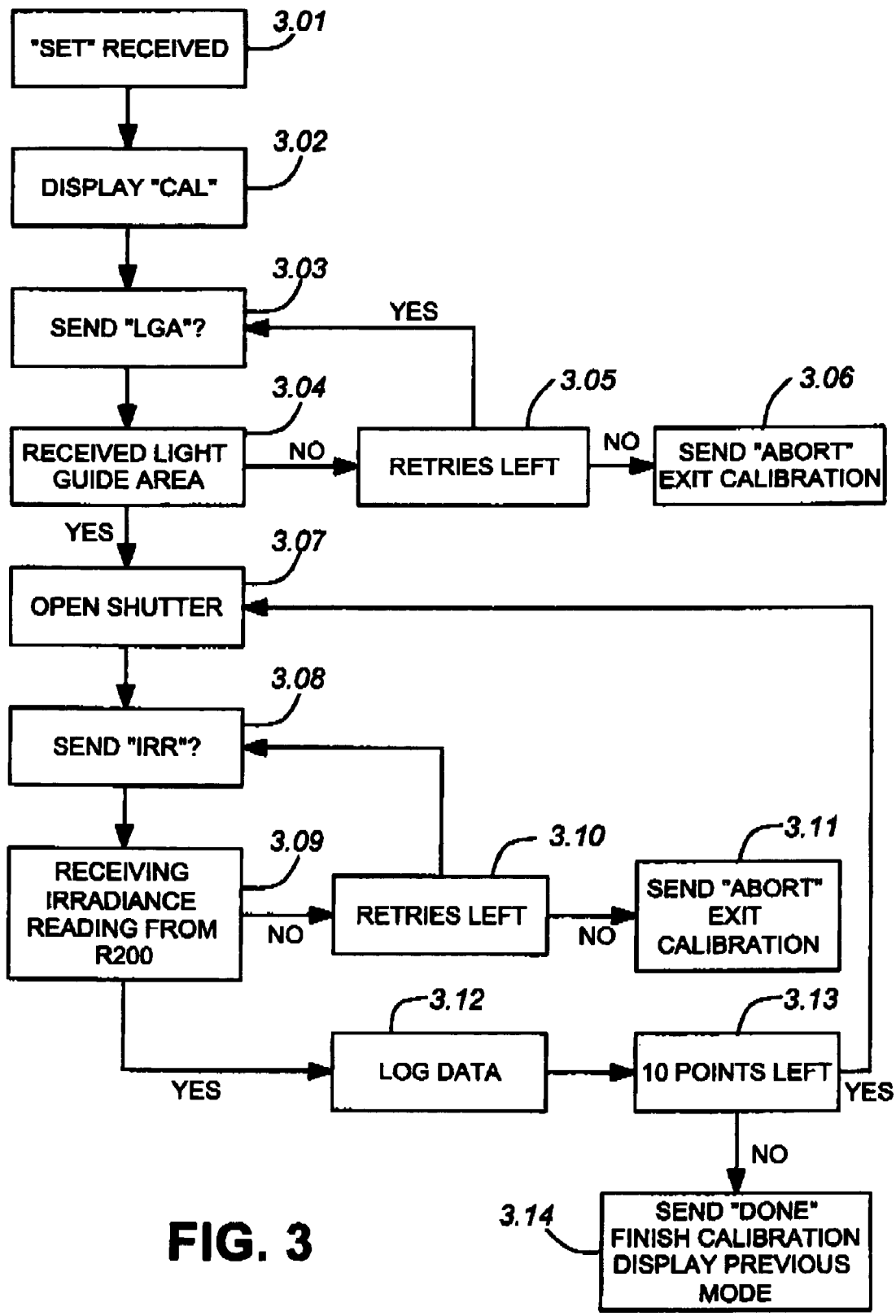
FIG. 3 is a flowchart depicting the method steps performed by the light delivery device during its calibration.

Calibration is performed by coupling the light guide 26 to the optical input port 40 of the radiometer 38 and initiating automatic performance of a series of irradiance measurements at ten predetermined PWM duty. This calibration procedure will now be described with reference to Table II below and the flowchart shown in FIG. 3, the Table steps being referenced T1, T2, . . . and the flowchart steps being referenced 3.01, 3.02, . . . and so on. It should be noted that the flowchart depicts only part of the calibration process in terms of functions of the light delivery device 10, whereas Table II illustrates functions of both the light delivery device 10 and the radiometer 38. In the following description, the various commands or messages will be described as being exchanged by the radiometer 38 and the light delivery device 10, but it will be appreciated that it is their respective control units 28 and 49 that communicate via the Serial links.

With the optical port and data port of the radiometer 38 coupled to the light guide and the dataport of the light delivery device 10, the radiometer 38 checks the state of its "CAL" pushbutton and, if it is idle (i.e. not pushed), repeats the check periodically. In step T1, the user initiates communications between the radiometer 38 and the light delivery device 10 by pressing the CAL pushbutton to select the calibration mode of the radiometer 38, whereupon the radiometer 38 attempts to set up communications with the light delivery device 10 via the Serial link. The light delivery device 10 responds with a "ready" command (step T2), at which point communications have been established. In step T3, the control unit 48 requests the serial number of the light delivery device 10 which transmits it in step T4. On receipt of the serial number, the radiometer 38 stores it in its memory 50.

In step T5, the radiometer 38 sends a "SET" command to the light delivery device 10. This "SET" command may be a desired irradiance level to which the light delivery device 10 is to be set for a subsequent curing operation, but nevertheless will cause the light delivery device 10 to enter the calibration mode and, in step 3.02 (see FIG. 3), display a "CAL" icon. In step T6/3.03, the light delivery device 10 sends the radiometer 38 a command requesting the light guide area (LGA). In step 3.04, the light delivery device 10 monitors for receipt of the LGA and repeats the request (step 3.05). If a predetermined number of requests fail to illicit the LGA, in step 3.06 the light delivery device 10 sends an "about" command and exits the calibration process. If desired, of course, the radiometer could transmit the dimensions (e.g., diameter) rather than the LGA, and the light delivery device 10 could compute the area itself, or simply apply a suitable scaling factor when calculating irradiance.

If, in step T7, the radiometer 38 transmits the light guide area (LGA), having previously determined it by using the colorimeter 58, as described above, to identify the adapter colour, then looking up the corresponding diameter in memory 50, and calculating the corresponding area On receipt of the area in step 3.04, the light delivery device 10 adjusts the parameters of the control signal from the PWM signal generator 18, in step T8/3.07, to the first of the ten predetermined settings corresponding to preprogrammed calibration set points, switches on the LED array and leaves shutter open. The predetermined parameters of the control signal for each PWM setting for the various calibration points are programmed into the memory 30 of the light delivery device 10.

In step T9, the radiometer 38 measures the power of the light received by its thermopile 44 and, using the light guide area (LGA), calculates the corresponding irradiance as $W/cm^2$ (by dividing the power by the light guide area). After a certain "setting time" to allow the reading to stabilize, the light delivery device 10 sends a request to the radiometer 38 for the irradiance reading (step T10/3.08). In step T11, the radiometer 38 sends the irradiance reading to the light delivery device 10 and also stores this irradiance reading in its own memory 50, along with the serial number of the light delivery device 10, the corresponding power as measured by its thermopile 44, the calibration date and the current time (in real time as opposed to "lamp" hours or service hours), as shown in Table I.

On receipt of the irradiance reading (in step 3.09), the light delivery device 10 stores it in its own memory 30 (step 3.12) in association with the control signal parameter and the digital representation $S_O$ of the intensity reading $I_0$ of the light entering the light guide 26 via optical port 24. In step 3.13, the light delivery device 10 determines whether or not irradiance readings have been taken for all ten calibration points. If they have not, it returns to step 3.07, adjusts the control signal parameters to the next calibration point, and repeats steps T9-T12 and 3.08-3.13 for the new calibration point. This cycle repeats until step 3.13 indicates that all ten irradiance readings and ten corresponding intensity levels have been measured, whereupon, in step T14/3.14, the light delivery device 10 sends a "Done" command to the radiometer 38 and returns to its previous display mode.

The light delivery device 10 also determines whether or not the received irradiance values are valid. It does so by comparing each received irradiance value (after the first) to the previous one and ensuring that they differ from each other by a predetermined amount, i.e. as a percentage. If any of the received values is determined to be invalid, the calibration (CAL) procedure is aborted and an ABORT command sent to the radiometer.

On receipt of the "Done" command, in step T15 the radiometer 38 exits the calibration sequence and returns to normal operation.

Once the light delivery device 10 has obtained the ten irradiance measurements, they are associated in the data memory 30 of the light delivery device 10 with ten corresponding values of the digital signal $S_0$ representing the intensity $I_0$ detected by the photodetector 64 (i.e. in the feedback control system) and the ten control signal parameter values, such as percentage duty cycle.

The control unit 28 performs a "best fit" algorithm, e.g., a ten point cubic-spline, twice, once upon the ten pairs of irradiance and digital intensity values and once upon the ten pairs of irradiance and control signal parameter values. In each case, the control unit 28 determines coefficients of the spline function linking control signal parameter with irradiance and intensity so that, when the light delivery device is being set to deliver a "desired" irradiance level, the inputted desired irradiance level $I_{LG}$ can be used to determine both a corresponding control signal parameter and a corresponding intensity level $I_0$. For both iterations of the spline, input arrays X (e.g. irradiance level) and Y (e.g. control signal parameter or intensity level) are used to determine coefficients A, B, C and D as follows:

$$y = Ay_i + By_i+1 + Cy_i'' + Dy_i''+1 \quad (1)$$

and the coefficients are given by $$A = \frac{x_{i+1} - x}{x_{i+1} - x_i} \quad (2)$$

$$B = 1 - A \quad (3)$$

$$C = \frac{1}{6}(A^3 - A)(x_{i+1} - x_i)^2 \quad (4)$$

$$D = \frac{1}{6}(B^3 - B)(x_{i+1} - x_i)^2 \quad (5)$$

Therefore, in order to obtain a PWM duty cycle setting, or other control signal parameter or intensity level (e.g. "y") that corresponds to a particular irradiance level (e.g. "x"), the control unit 28 computes the coefficients according to formulas 2, 3, 4 and 5 and subsequently computes the desired value from formula 1 as given above.

It should be noted that the linearity of the fit will depend upon the type and configuration of LED array used, the LED Driver and dimmer module, shutter (where applicable), and so on. Typically, at lower irradiance values where the signal-to-noise ratio is lower and where parameters may be set less accurately, a large number of points will be interpolated. Coefficients calculated using the spline functions are used for subsequent determinations of the a PWM duty cycle parameter or other control signal parameter required to produce a desired output irradiance (at the end of the light guide) when the delivery device is in subsequent use.

If the calibration sequence was initiated by the radiometer 38 downloading a new "desired" irradiance level, the light delivery device 10 now will set the control signal parameter to the value that when the splines are taken into account, will produce the desired irradiance level at the output of light guide 26, as will be described in more detail later.

Following calibration of the light delivery device 10, the data memory 50 in the radiometer 38 stores ten data entries against the serial number for that light delivery device 10, as illustrated in Table I. Each row constitutes a calibration data record and includes entries for the date and time the measurement was made, the serial number (S/N) of the light delivery device 10, the power in watts (W), as measured by the thermopile 44, and the irradiance in $W/cm^2$ (as calculated by the radiometer 38 from the current power measurement and the cross-sectional area of the current light-guide). An extra column for input channel number is optional and indicates whether the radiometer 38 is being used with an external radiometer 38 coupled to its RIC port 84 (channel 1) or the thermopile 44 (channel 0). The radiometer 38 could, of course, still store other readings for the same light delivery device from previous calibrations, but they would have a different time/date.

The radiometer 38 then can be coupled to one or more other light delivery devices, in turn, and the calibration process repeated, the group of calibration data records for the other delivery devices being stored as before, but in conjunction with the different serial numbers.

The calibration data records for all of the light delivery devices stored by the radiometer 38 are accessible to an external computer via the second serial port 34' using suitable command software or via it own display 82. Thus, at suitable intervals, for example daily or weekly, the radiometer 38 may download the data to the external computer 86 for statistical analysis, quality control purposes, archiving, and so on. The data records can be displayed using the same graphical user interface.

In a production environment, where several light delivery devices have been calibrated as described above, the radiometer 38 also can be used to set several light delivery devices to the same predetermined irradiance setting. Preferably, whenever a delivery device is being set to a new irradiance level, it will automatically perform the calibration process, so its light guide will already be attached to the radiometer 38. Thus, having been calibrated, the first delivery device is adjusted manually, i.e., using the user interface pushbuttons, so as to set the irradiance measured by the radiometer 38 to a desired (optimum) irradiance for a particular process.

Once the radiometer 38 reads this optimum or "desired" irradiance value, the user presses and holds the STORE button on the radiometer 38 for 5 seconds to store the "desired" irradiance setting of the first light delivery device 10 into the memory 50 of the radiometer 38.

To set the other light delivery devices to the same irradiance set point, the radiometer 38 is connected to each of them in turn, specifically by connecting its optical port to their light guides and its data port to their data ports. Even if the other light delivery devices have been calibrated, as described above, quite recently, the calibration will be repeated. The user presses the "CAL" button on the radiometer 38 which then downloads the "desired" irradiance to the light delivery device control unit 48 via the data ports.

TABLE I

| Date and time | Serial # | Power (W) | Irradiance (mW/cm²) | Input Channel |
|---|---|---|---|---|
| 2004-01-01, 1:00:00 pm | 00001 | 5.0 | 25000 | 0 |
| 2004-01-01, 1:00:04 pm | 00001 | 5.1 | 25500 | 0 |
| 2004-01-01, 1:00:08 pm | 00001 | 5.2 | 26000 | 0 |
| 2004-01-01, 1:00:12 pm | 00001 | 5.3 | 26500 | 0 |
| 2004-01-01, 1:00:16 pm | 00001 | 5.4 | 27000 | 0 |
| 2004-01-01, 1:00:20 pm | 00001 | 5.5 | 27500 | 0 |
| 2004-01-01, 1:00:24 pm | 00001 | 5.6 | 28000 | 0 |

TABLE I-continued

| Date and time | Serial # | Power (W) | Irradiance (mW/cm²) | Input Channel |
|---|---|---|---|---|
| 2004-01-01, 1:00:28 pm | 00001 | 5.7 | 28500 | 0 |
| 2004-01-01, 1:00:32 pm | 00001 | 5.8 | 29000 | 0 |
| 2004-01-01, 1:00:36 pm | 00001 | 5.9 | 29500 | 0 |
| 2004-01-01, 1:00:40 pm | 00001 | 6.0 | 30000 | 0 |
| 2004-01-01, 1:06:04 pm | 00002 | 5.0 | 25000 | 0 |
| 2004-01-01, 1:06:08 pm | 00002 | 5.1 | 25500 | 0 |
| . | ... | ... | ... | ... |

As discussed, above, this automatically causes the light delivery device 10 to perform the calibration sequence described above and only when that has been completed will the light delivery device 10 set its output level, i.e., PWM duty cycle or other control signal parameter, to achieve the desired irradiance. This process is repeated for each light delivery device of the group.

It should be noted that the feedback control loop (22, 64, 66, 28, 20, 16) that compensates for variations in the output of LED array 60 will operate in "real time".

Whenever a new desired irradiance level is being set, the control unit 28 will determine the corresponding control signal parameters and intensity level which correspond to the desired irradiance at the output end of the light guide, derived using the spline coefficients, and then adjust parameters of the control sign to change the duty cycle accordingly.

TABLE II

| Step | Radiometer | Light delivery device |
|---|---|---|
| 1 | User presses CAL button on radiometer 38 which initiates communications with light delivery device via a wired or wireless port | |
| 2 | | Light delivery device 10 sends a "ready" command as communications with radiometer 38 have now been opened. |
| 3 | Radiometer 38 sends a command for light delivery device 10 unit serial number. | |
| 4 | | Light delivery device 10 sends the unit serial number to radiometer 38. |
| 5 | Radiometer 38 sends a "SET" command to light delivery device 10 to select the first one of a series of predetermined control signal parameters. | |
| 6 | | Light delivery device 10 sends a command to radiometer 38 requesting light guide dimensions. |
| 7 | Radiometer 38 sends the previously determined dimensions of the light guide to light delivery device 10. | |
| 8 | | The light delivery device 10 sends a controls signal from the dimmer module to the LED array having control signal parameters selected to provide the first one of the predetermined intensity levels. |
| 9 | The radiometer 38 measures power and calculates the irradiance using the light guide area. | |
| 10 | | The light delivery device 10 sends a request to the radiometer 38 for the irradiance value. |
| 11 | The radiometer 38 sends the irradiance value to the light delivery device 10. | |
| 12 | The radiometer 38 stores the following data: Serial number of current light delivery device 10 Current power in W Current irradiance in W/cm² Current date and time. | |
| 13 | Repeat steps 9-12 for the other 9 predetermined control signal parameters. | |
| 14 | | When the delivery device has completed the calibration point, it sends a "Done" command to the radiometer 38. |
| 15 | Radiometer 38 exits calibration sequence and returns to normal operation. | |

The control unit 28 then compares the "desired" digital value $S_0'$ of the intensity $I_0'$ now being measured at the photodetector 64 with the "calibrated" digital value, as determined using the second spline coefficients. If the "desired" digital value is different, as would be likely if the output of the LED array 60 had changed (increased or decreased in intensity) since the previous calibration, the control unit 28 changes the PWM duty cycle gradually until the "desired" digital intensity value is equal to the "calibrated" digital intensity value, thereby compensating for any changes in the light intensity delivered by the light source and ensuring that the light leaving the far end of the light guide 26 has the desired irradiance level.

Preferably, when establishing communications, the radiometer acquires from the LED array a unique identifier, such as its serial number, and associates the irradiance readings with that unique identifier. Each LED array may have its own memory, which is used to store LED-specific information, which may include, a serial number and information on the LED type, and may also store a calibration table containing a relationship between a dimming signal setting, and an output power level. A control module may select the appropriate control signal, i.e., dimming signal setting, for each LED array to ensure each LED array of a group is set to, e.g., the same intensity level and have power outputs which fall within a specific range. Alternatively the intensity of each LED array may be individually controlled, or controlled using different grouping rules to select appropriate control signals (dimming signals) to provide desired intensity levels and power outputs from each LED array. Thus the method of calibration is adaptable to multiple LED arrays of different configurations using a variety of grouping rules.

It will be appreciated that various alternatives and modifications are feasible without departing from the scope of the present invention. Thus, the solid state light source 12 may comprise other known devices, e.g., individual light emitting diodes (LEDs) and groups of LEDs and multiple LED array devices of different configurations, and other solid state light sources which may be similarly controlled electronically, and capable of generating UV or visible light, or alternatively a microwave source, depending on requirements of the application.

Generally, the type of light source 12 will be selected according to the application. It should be appreciated that a photo-sensitive material might require light having wavelengths and intensity that are completely different from those required for performing phototherapy, printing and curing applications.

In applications where it is not necessary to deliver a focussed or collimated beam of the light, the fiber optic cable or liquid light guide can be omitted. For example, where the light source 12 comprises a LED array or group of LED arrays which illuminates a defined area, a light guide may not be required.

Figure 4:
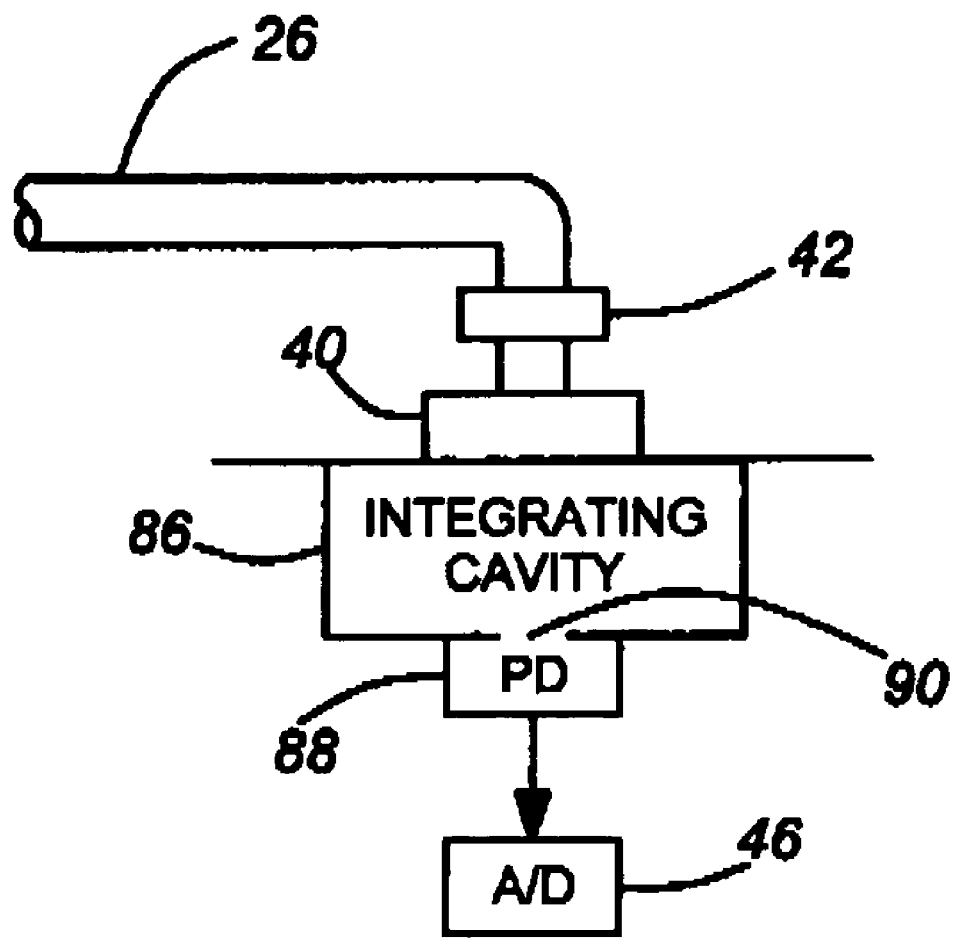
FIG. 4 is a partial schematic diagram illustrating a modification to the radiometer.

The detection means 44 could comprise additional optical elements, such as an integrating cavity and the thermopile 44 shown in FIG. 1 could be replaced by some other kind of photodetector, for example a photodiode. Thus, FIG. 4 shows an alternative detection means comprising an integrating cavity 86, which receives and integrates the light from light guide 26 via port 40, and a photodiode 88 for detecting light at an output port 90 of the integrating cavity and supplying the corresponding electrical signal to A/D converter 46. It should be appreciated that the "desired" irradiance setting could instead be entered into the light delivery device 10 using its own user interface and display 32, or by means of a similar interface displayed on an external computer connected to the serial data port of the light delivery device 10.

It is envisaged that the user interface and the display unit 32 could be adapted to allow the user to initiate the calibration of the light delivery device 10.

It will be appreciated that the data could be transferred between the radiometer 38 and the light delivery devices or external computer using alternatives to the serial protocols e.g., RS232, such as USB, GPIB, and so on. It should be noted, however, that wireless connections have certain advantages over data cables because they simplify connection of the radiometer 38 to each of several light delivery devices in turn, leading to time savings.

It should also be noted that a variety LED Driver and Distributed Dimmer Modules capable of control signal generation of various configurations and types could be used, and based on analog or digital control signals.

The bandpass filter 14 could be any appropriate optical filter and could be integrated with other components of the light delivery device 10.

It should also be noted that while control signal parameters for ten calibration points are used for the calibration process in the above description, parameters for any number of intensity levels maybe used. The accuracy of the calibration will, of course, increase with the number of different sets of control signal parameters for intensity levels used, and their distribution across the range of operation.

As mentioned above, the light delivery device 10 could be used in relative mode, i.e., without using the radiometer to associate control signal parameters for intensity levels with irradiance values using the spline function. Even so, it would still be possible to use the spline function to calibrate the internal feedback loop that compensates for degradation of the LED arrays 60, . . . 60n. In that situation, of course, there would be no series of irradiance measurements so the spline would be applied to associate the intensity measurements with a percentage duty cycle of the control signal or directly with the other control signal parameters.

The invention is not limited to the above described system and method, or indeed to systems and methods for applying light to photosensitive materials to initiate printing, curing, drying, hardening or other photosensitive reaction, but comprehends systems and methods for use in other applications, for example general illumination, machine vision, photobiology, photodynamic therapy/phototherapy, microscopy, and general medical applications, including diagnostic imaging.

Although various preferred embodiments of the present invention have been described in detail, it will be appreciated by those skilled in the art that variations may be made without departing from the spirit of the invention or the scope of the appended claims.

The invention claimed is:

1. A method of setting an output level of a light delivery device (10) that comprises solid state light-emitting means (12), light output means (24; 24, 26) for delivering emitted light to a site to be irradiated, intensity control means (16) for generating a control signal for adjusting at least the intensity of the delivered light, and a memory unit (30) for storing data including parameters indicative of intensity/power level, the light output means (24;24, 26) being temporarily connected to a separate radiometer (38) having means for detecting power levels of the delivered light, the light delivery device (10) and the radiometer (38) having respective control means (28, 48) and data communications means (34, 36, 54, 56) for communicating data therebetween, the method comprising a calibration sequence comprising the steps of:
  (i) with the light output means (24; 24, 26) coupled to the radiometer (38), establishing data communications between the control means (48) of the radiometer (38) and the control means (28) of the light delivery device (10);
  at the light delivery device (10):
  (ii) adjusting the intensity control means (16) successively to set parameters of the control signal corresponding to each of a series of predetermined intensity levels;
  at the radiometer (38):
  (iii) measuring a series of actual output radiance levels delivered by the light output means (24; 24, 26), each for a respective one of said predetermined intensity levels;
  (iv) transmitting the actual output irradiance levels to the light delivery device (10);
  at the light delivery device (10):
  (v) associating each of the actual output irradiance level measurements with the corresponding control signal parameters in said memory unit.

2. A method according to claim 1, wherein the solid state light-emitting means (12) comprises LEDs of at least one LED array, and the intensity control means (16) comprises an LED array driver and a dimmer control module for generating a control signal having control signal parameters for adjusting at least the intensity of the delivered light, and wherein the step of adjusting the intensity control means (16) successively to each of a series of predetermined intensity levels comprises setting parameters of the control signal generated by the dimmer control module of the intensity control means (16) successively to each of a series of different control signal parameters associated with at least the intensity of the delivered light.

3. A method according to claim 2, wherein the dimmer module generates a pulse width modulated control signal and the adjusting of the intensity control means (16) successively to each of a series of predetermined intensity levels comprises selecting a duty cycle of the control signal associated with a predetermined intensity level.

4. A method according to claim 2, comprising generating a control signal for selectively controlling individual LEDs and groups of LEDs of each of a plurality of LED arrays.

5. A method according to claim 2, comprising setting the control signal parameters of a control signal for a respective one of a plurality of LED arrays in a group to set the intensity level of each LED array in the group to the same level.

6. A method according to claim 1, further comprising the step of:
(vi) applying a best fit algorithm to the actual irradiance level measurements and corresponding predetermined control signal parameters and using the best fit parameters to select subsequent desired output irradiance levels.

7. A method according to claim 1, wherein, in a subsequent step of setting the light delivery device (10) to deliver a desired output irradiance level, the intensity level of light downstream of the output of the intensity control means (16) is measured, compared with a reference, and the intensity control means (16) adjusted to set control signal parameters to correct for any differences between the measured intensity level and the reference.

8. A method according to claim 6, further comprising the steps of:
obtaining for each of said series of predetermined control signal parameters associated with an intensity level of the solid state light emitting means, a corresponding series of measurements of intensity level of light downstream of the output of the intensity control means (16),
applying a best fit algorithm to the actual irradiance level measurements and corresponding parameters;
applying a best fit algorithm to the actual intensity level measurements and said actual irradiance level measurements;
in a subsequent intensity level setting step, setting the control signal parameters to provide a desired intensity level, measuring the said actual intensity level again, comparing the measured-again intensity level with the intensity level for that desired irradiance level according to the best fit algorithm, and adjusting the intensity control means (16) to set control signal parameters to correct for any differences.

9. A method according to claim 1, wherein when establishing communications, the radiometer (38) acquires from the light delivery device (10) a unique identifier, such as its serial number, and stores the irradiance measurements in association with said unique identifier in a memory unit (50).

10. A method according to claim 9, wherein each of the irradiance measurements is stored in association with temporal information identifying when such measurement was made.

11. A method according to claim 1, the light output moans comprising a light guide (26) coupled to an optical output port (24) of the light delivery dice (10), the method further comprising the step of determining the dimensions of the light guide (26) and using the measured power and the effective cross-sectional area, derived from the dimensions, to compute the irradiance of the delivered light.

12. A method according to claim 10, wherein the computation of the irradiance is performed at the radiometer (38).

13. A method according to claim 11, wherein the radiometer (38) stores effective dimensions of a plurality of different types of light delivery means, the light delivery means of a particular type having the same effective cross-sectional area, and being associated with an indicator unique to that type, and the step of determining the active cross-sectional area includes the steps of detecting a said unique indicator of said light delivery means connected to the optical input port, using the detected indicator to retrieve the effective dimensions for that light delivery means from storage and calculating the cross-sectional area from that effective dimensions.

14. A method according to claim 13, wherein the unique indicator is colour of a colour-coded adapter (42) specific to the type of light delivery means (26) and the step of detecting said unique indicator includes the step of determining the colour of the colour-coded adapter (40) connecting the light delivery means (26) to the optical input port (40).

15. A method according to claim 1, further comprising the step of repeating the calibration sequence for each of a plurality of other similar light delivery devices (10) and setting the plurality of other similar light delivery devices to the same output level by coupling the radiometer (38) to each of the light delivery devices (10) in turn, outputting from the radiometer (38) to the control means (28) of the light delivery device (10) a desired irradiance value previously stored in the radiometer (38); and storing the light irradiance value in the memory (30) of the light delivery device (10), each light delivery device (10) using the stored irradiance value for subsequent operation.

16. A method according to claim 15, wherein the desired irradiance is obtained by the prior step of measuring an actual irradiance level outputted by one of the light delivery devices, or a similar light delivery device, adjusting the light delivery device until the actual irradiance level is acceptable, and storing the accepted irradiance level as said desired irradiance level for supplying to the other light delivery devices.

17. A method according to claim 1, wherein the data communications link is established by way of wireless input/output ports of the light delivery device (10) and radiometer (38), respectively.

18. A method of setting respective output light irradiance levels of a plurality of light delivery devices to the same irradiance level using the same radiometer, each light delivery device comprising solid state light-emitting means, output means for supplying the emitted light to a site to be irradiated, intensity control means (16) generating a control signal for adjusting at least the intensity of the delivered light, a memory unit for storing parameters indicative of intensity levels and control means for controlling the intensity control means, the radiometer having data storage means for storing data including light irradiance values, the radiometer and light delivery devices having data communications means for communicating data therebetween, the method comprising the steps of:
(i) adjusting a first light delivery device to set parameters of the control signal to deliver a desired irradiance level at its output means;
(ii) temporarily coupling the radiometer to the output means of the first light delivery device and measuring said desired irradiance level;
(iii) storing said desired irradiance level in the memory of the radiometer;
(iv) temporarily coupling the radiometer to the output means of at least a second such light delivery device, and transmitting said desired irradiance level to said second delivery device via said data communications means; and
(v) storing the light irradiance value in the memory of the second light delivery device for future use in normal operation.

19. A method according to claim 17, further comprising the prior step of calibrating each of the light delivery devices with the radiometer (38) so that irradiance levels correspond to control signal parameters.

20. A method according to claim 18, wherein the data communications link is established by way of wireless input/output ports of each light delivery device and the radiometer (38), respectively.

21. A method of setting respective output light irradiance levels of a plurality of light delivery devices (10) to the same irradiance level using the same radiometer (38), each light delivery device (10) comprising light-emitting means (12), output means (24; 24, 26) for supplying the emitted light to a site to be irradiated, intensity control means (16) generating a control signal having control signal parameters for adjusting the irradiance of the delivered light, a memory unit for storing irradiance levels, and control means (28) for controlling the intensity control means (16), the radiometer (38) having data storage means (50) for storing data including light irradiance values, the method comprising the steps of:
- temporarily coupling the radiometer (38) to the output means of each light delivery device in turn, and outputting to each said light delivery device a control signal having parameters selected to provide a desired irradiance level previously stored in the memory of the radiometer (38); and
- storing the light irradiance value in the memory unit of each said light delivery device (30) for future use in normal operation.

22. A method according to claim 21, wherein the radiometer is coupled to the light delivery device by means of a wireless data communications link.

23. A radiometer (38) for use in setting output light delivered by at least one light delivery device (10) to a desired light irradiance level, said at least one light delivery device comprising light emitting means (12), light output means (24; 24, 26) for supplying the emitted light to a site to be irradiated, intensity control means (16) for generating a control signal for adjusting the irradiance of the delivered light, a memory unit for storing irradiance levels, and data communications means (28, 34, 36), the radiometer (38) comprising:
- means for measuring an irradiance level of light delivered by said light output means of said light delivery device;
- data communications means (48, 54, 56) complementary to the data communications means (28, 34, 36) of the light delivery device; and
- control means (48) for establishing data communications with a light delivery device (10) coupled hereto and for outputting to said light delivery device (10) a control signal having signal parameters for said desired light irradiance value retrieved from said memory via the data communications means.

24. A radiometer according to claim 21, fiber comprising storage means (50) for storing a plurality of said desired irradiance values in association with a unique identifier, for example serial number, of a said light delivery device (10), and wherein the control means is operable to obtain said unique identifier from said light delivery device via said data communications link.

25. A radiometer according to claim 23, further comprising data communication means for communication stored data to an external computer.

26. A radiometer according to claim 23, wherein the data communications means is wireless.

27. A radiometer according to claim 23, further comprising means for detecting an identifier of a light output means connected thereto, said identifier indicating that the light output means has a particular dimension, the control means being operable to use the identifier to determine the cross-sectional area and use the cross-sectional area and measured power to compute the irradiance of the delivered light.

28. A radiometer according to claim 27, wherein the identifier is the colour of a colour-coded adapter for connecting the light output means to the radiometer, and the detecting means is configured to detect the colour of the adapter and supply colour coordinates to the control unit, the memory unit storing colours and corresponding dimensions or areas of the light output means.

29. A radiometer according to claim 28, wherein the detecting means comprises a colorimeter.

30. A light delivery device comprising solid state light-emitting means, light output means for delivering the emitted light to a site to be irradiated, intensity control means (16) comprising a dimmer control system for adjusting irradiance of delivered light; and control means for controlling the intensity control means and for communicating with an external radiometer, the control means being operable to adjust the intensity, successively, to a plurality of intensity levels and, for each intensity level, communicate with the radiometer to obtain from the radiometer a corresponding series of actual irradiance levels measured by the radiometer and store each irradiance value in a memory unit in association with the corresponding intensity level.

31. A light delivery device according to claim 30, wherein the solid state light emitting means comprises LEDs of an LED array, and the intensity control means (16) comprises an LED array driver, and dinner control module (18) for generating a control signal for having parameters selected to set the intensity level of the optical output of the LED array, the stored parameters associated with each of a series of intensity levels.

32. A light delivery device according to claim 31, wherein the control means is operable to apply a best fit algorithm to the actual irradiance level measurements and corresponding aperture settings and use the best fit aperture settings to select subsequent desired output irradiance levels.

33. A light delivery device according to claim 31, further comprising means for measuring the intensity level of light downstream of the output of the intensity control means (16), the control means being operable to associate a series of intensity measurements with said series of irradiance measurements and, when subsequently setting the intensity of light outputted by the light delivery device (10) to deliver a desired output irradiance level, set the intensity to an initial setting corresponding to the desired irradiance level, measure the actual intensity level and compare such actual intensity level with the associated intensity level and adjust the intensity control means (16) to correct for any differences between the measured actual intensity level and the associated intensity level.

34. A light delivery device according to claim 33, further comprising means for measuring the intensity level of light downstream of the output of the intensity control means (16), the control means being operable to associate a series of intensity measurements with said series of irradiance measurements and perform a best fit algorithm to associate intensity measurements with irradiance measurements and, when subsequently setting the intensity control means of the light delivery device (10) to deliver a desired output irradiance level, set the intensity to an initial setting corresponding to the desired irradiance level, measure the actual intensity level and compare such a intensity level with the associated intensity level and adjust the intensity control means (16) to correct for any differences between the measured actual intensity level and the associated intensity level.

35. A light delivery device according to claim 31, wherein the dimmer module (18) is adjustable between a completely switched off state and a variety of on states, the control means

(28) being operable to control the PWM signal Generator means (18) from a switched off state to a selected one of the on states, and back to the switch off state to determine exposure period.

36. A light delivery device according to claim 31, wherein the control means further comprises a shutter.

37. A light delivery device comprising solid state light-emitting means (12), light output means (24; 24, 26) for delivering the emitted light to a site to be irradiated, intensity control means (16) comprising a device driver and a dimmer module for generating a control signal for the solid state light emitting means for adjusting irradiance of delivered light, detection means for detecting intensity of light downstream of the output of the intensity control means and control means (28) for controlling the intensity control means (16), wherein the control means (28) is operable to:

monitor the detection means and determine, for each of series of predetermined intensity level settings, a corresponding series of measurements of intensity level of light downstream of the output of the intensity control means (16), apply a best fit algorithm to the actual intensity level measurements and said intensity level setting; and in a subsequent intensity level setting step, adjust the intensity level to the desired setting, measure the said intensity level again, compare the measured-again intensity level with the intensity level for that intensity level setting according to the best fit algorithm, and adjust the intensity control means (16) to correct for any differences.

* * * * *